(12) United States Patent
Wilhelm et al.

(10) Patent No.: US 7,691,375 B2
(45) Date of Patent: Apr. 6, 2010

(54) ADJUVANT THERAPHY OF G250-EXPRESSING TUMORS

(75) Inventors: Olaf Wilhelm, Munich (DE); Sven Warnaar, Leiden (NL)

(73) Assignee: Wilex AG, Munich (DE)

( * ) Notice: Subject to any disclaimer, the term of this patent is extended or adjusted under 35 U.S.C. 154(b) by 287 days.

(21) Appl. No.: 11/630,170

(22) PCT Filed: Jun. 29, 2005

(86) PCT No.: PCT/EP2005/006994

§ 371 (c)(1),
(2), (4) Date: Dec. 20, 2006

(87) PCT Pub. No.: WO2006/002889

PCT Pub. Date: Jan. 12, 2006

(65) Prior Publication Data

US 2007/0207157 A1    Sep. 6, 2007

Related U.S. Application Data

(60) Provisional application No. 60/584,679, filed on Jul. 2, 2004.

(51) Int. Cl.
*A61K 39/395* (2006.01)
*C07K 16/00* (2006.01)
(52) U.S. Cl. ............. 424/133.1; 424/130.1; 424/277.1; 424/138.1; 530/387.1; 530/388.8
(58) Field of Classification Search ........................ None
See application file for complete search history.

(56) References Cited

U.S. PATENT DOCUMENTS

2003/0027994 A1 * 2/2003 Anderson et al. ...... 530/388.15

FOREIGN PATENT DOCUMENTS

| WO | 93/18152 | * | 9/1993 |
| WO | 02/062972 | * | 8/2002 |
| WO | WO 02/062972 A | | 8/2002 |
| WO | WO 03/068924 A | | 8/2003 |
| WO | WO 2004/002526 A | | 1/2004 |

OTHER PUBLICATIONS

Saarnio et al J. Hepatol. vol. 35 p. 643 (2001).*
Bleumer et al European Urology Supplements vol. 1 p. 112, (2002).*
Uemura et al British Journal of Cancer vol. 81 p. 741 (1999).*
Grabmaier et al Intl. J. Cancer vol. 85 p. 865 (2000).*
Steffens et al., "Phase I Radioimmunotherapy of Metastatic Renal Cell Carcinoma with 131I-labeled Chimeric Monoclonal Antibody G250", Clinical Cancer Research, vol. 5, 1999, pp. 3268S-3274S.
Moch et al., "Genetic Abberrations Detected by Comparative Genomic Hybridization are Associated with Clinical Outcome in Renal Cell Carcinoma", Cancer Research, vol. 56, 1996, pp. 27-30.
Oosterwijk et al., "Antibody Localization in Human Renal Cell Carcinoma: A Phase I Study of Monoclonal Antibody G250", Journal of Clinical Oncology, vol. 11, No. 4, Apr. 1993, pp. 738-750.
Grabmaier et al., "Molecular cloning and immunogenicity of renal cell carcinoma-associated antigen G250," International Journal of Cancer, vol. 85, 2000, pp. 865-870.
Jongmans et al., "Targeting of adenovirus to human renal cell carcinoma cells", Urology, vol. 62, No. 3, 2003, pp. 559-565.
Bismar et al., "Quantification of G250 mRNA expression in renal epithelial neoplasms by real-time reverse transcription-PCR of dissected tissue from paraffin sections", Pathology, vol. 35, No. 6, 2003, pp. 513-517.
Brouwers et al., "Pharmacokinetics and tumor target of 131I-labeled F(ab')2 fragments of the chimeric monoclonal antibody G250: preclinical and clinical pilot studies", Cancer Biothery and Radiopharmaceuticals, vol. 19, No. 4, 2004, pp. 466-477.
Dorner, G. et al., "Successful Treatment of Prostatic Cancer with Orally Active Depot Estrogen Ethinylestradiol Sulfonate (Turisteron), Exp. Clin. Enocrinol. vol. 86, No. 2, 1985, pp. 190-195.
de-Jong Busnac et al., Ophthalmologic Complications of Low-Dosage Tamoxifen in the Treatment of Breast Carcinoma, PubMed—indexed for Medline, 1989. (Abstract only).
Boccon-Gibod, Are Non-Steroidal Anti-Androgens Appropriate as Monotherapy in Advance Prostate Cancer?, European Urology Clinical Paper, 1998:33:159-164.
N. Kawata, et al.: "Immunological effect of recombinant interferon-gamma in renal cell carcinoma," PubMed—indexed for Medline, Jun. 1993: 39(6): 511-5. (Abstract only).
"Eine Neue Antikorpoer—Therapie fur Nierenzellkarzinome," Mar. 29, 2006, 3 pages, XP002374806.

* cited by examiner

*Primary Examiner*—Sheela J Huff
(74) *Attorney, Agent, or Firm*—Rothwell, Figg, Ernst & Manbeck, P.C.

(57) ABSTRACT

The invention relates to a method for the treatment of G250-antigen-expressing tumors, in particular renal clear cell carcinoma comprising the administration of G250-antigen-specific antibodies to high-risk patients diagnosed with non-metastasizing disease.

18 Claims, No Drawings

ADJUVANT THERAPHY OF G250-EXPRESSING TUMORS

This application is a 35 U.S.C. § 371 National Phase Entry Application from PCT/EP2005/006994, filed Jun. 29, 2005, and designating the United States, which claims the benefit of U.S. Provisional 60/584,679, filed Jul. 2, 2004.

The invention relates to a method for the treatment of G250-antigen-expressing tumors, in particular renal clear cell carcinoma comprising the administration of G250-antigen-specific antibodies as an adjuvant treatment modality to high-risk patients diagnosed with non-metastasising disease.

BACKGROUND OF THE INVENTION

The G250 antigen is closely associated with numerous carcinomas, of which renal cell carcinoma was one of the first documented cases. Therefore the G250 antigen was first described as a kidney cancer associated antigen (WO88/08854). Later it was found to be identical with the tumor associated antigen MN, a cell surface antigen with carbonic anhydrase activity, also referred to as CAIX. Normal G250 expression is found in gastric, intestinal and biliary mucosa where its physiological role resides in pH regulation. Besides its normal expression pattern G250 expression is found in cervical carcinomas (1), esophageal carcinomas (2), colorectal carcinomas (3), lung carcinomas (4), biliary (5) and clear cell renal cell carcinomas (RCC) (WO88/08854)

For RCC it is estimated that 41,325 new cases were diagnosed in the European Union in 1995, with 21,728 deaths resulting from the disease (EUCAN database, 1995). According to the United States Department of Health and Human Services about 30,000 new cases are diagnosed annually, with about 12,000 RCC related deaths (National Institute of Health, SEER Cancer Statistics Review, 1999).

About 50-60% of patients initially present with stage I or stage II disease, i.e. with localized RCC. After surgical removal of the primary tumor, these patients have a good prognosis with 5-year survival rates of 60-80% (stage I) and 40-60% (stage II) respectively. The remaining patients have less favorable prognosis. Although most patients with stage III disease, i.e. non-metastatic disease at the time of diagnosis (20-25% of total patients) will also undergo surgery. Their 5-year survival rate is only 20-40%. Such patients, despite the absence of clinically detectable tumor, are clearly at high risk of tumor recurrence. Patients with stage 1V (metastatic) disease (10-20% of total patients) have a 5-year survival rate of 0-20% (6). The stages can be defined in terms of the TNM classifications as given below in Table 1:

TABLE 1

Stage classification (31)

| Stage I | T1 | N0 | M0 |
|---|---|---|---|
| Stage II | T2 | N0 | M0 |
| Stage III | T3 | N0 | M0 |
| | T1, 2, 3 | N1 | M0 |
| Stage IV | T4 | N0, N1 | M0 |
| | every T | N2 | M0 |
| | every T | every N | M1 |

A prospective cohort study with outcome assessment in 814 patients was able to define five different categories with significant differences in both disease-specific and overall survival (7). These categories were converted to risk groups, defined by the 1997 TNM classification, Fuhrman's grade and ECOG performance status. Of 486 non-metastatic patients, 128 (27%) were low-risk, 190 (41%) were intermediate-risk, and 150 (32%) were high-risk patients. The 5-year overall survival between these groups differed significantly with 84%, 72% and 44%, respectively. In the high-risk group, 42,5% patients had a relapse within the first two years after nephrectomy. Fuhrman's nuclear grading can be defined as shown in Table 2 below.

TABLE 2

Fuhrman's Nuclear Grading (32)

| Grade 1 (GI) | Round, uniform nuclei approximately 10 microns in diameter (RBC is 6 microns) with minute or absent nucleoli |
| Grade 2 (GII) | Slightly irregular contours and diameters of approximately 15 microns with nucleoli visible at 400× |
| Grade 3 (GIII) | Moderately to markedly irregular nuclear contours and diameters of approximately 20 microns with large nucleoli visible at 100× |
| Grade 4 (GIV) | Nuclei similar to those of Grade 3 but also multilobular or multiple nuclei or bizarre nuclei and heavy clumps of chromatin |

Due to increased early diagnosis of RCC in patients and the high incidence of developing recurrent disease after surgery effective adjuvant therapies need consideration.

A cancer may appear to be localized—only growing in one spot—but it actually may have begun spreading. The cancer cells may have ventured out into the body, but in such small numbers that they cannot yet be detected. The patients may be symptom-free after primary treatment. Adjuvant therapy describes a way to target any remaining cancer cells that cannot be seen. Adjuvant therapies are used after primary treatments, such as surgery or radiation, to guard against cancer recurrences. Four main types of adjuvant therapy exist, which may be selected based on the type of cancer and its progression:

chemotherapy
hormone therapy
radiation therapy
immunotherapy.

The concept of adjuvant therapy is generally accepted and well established in several tumors such as breast and colon carcinoma. For nephrectomized patients who subsequently relapse, the median time to relapse is 15 to 18 months with 85% of relapses occurring within 3 years (8). No drug has been approved so far for the adjuvant treatment of RCC.

Pizzocaro et al. reported a large adjuvant study in RCC with 247 patients (9). Half of the patients received interferon-α (IFN-α) three times a week intramuscularly (i.m.) over a period of 6 months, starting within one month of surgery. The other half of the patients was observed only. The 5-year overall and event free survival probabilities showed no statistically significant difference. In 97 lymph node negative patients, a statistically significant harmful effect was seen in the treated group. In a small sub-group of 13 treated patients with pN2/pN3 (see below for classification) a protective effect could be observed when the 3-year cumulative probability of survival was reviewed. Due to the small size of this patient group, these data are not statistically significant. 55% of patients showed signs of toxicity caused by IFN-α and 28% required a dose reduction and/or suspension of the therapy. The results showed a higher death rate and a higher recurrence rate in the IFN treatment arm with 13% of the patient experiencing grade 4 toxicities.

The role of interleukin-2 (IL-2) in the adjuvant setting has not been finally defined yet. One study being conducted by the Cytokine Working Group in the U.S. is currently evaluating high dose IL-2 compared with observation only (10).

Due to the lack of positive study outcomes, combined with significant toxicities, the current standard of care after nephrectomy is close observation.

A phase III clinical study comprising an adjuvant therapy using an autologous vaccination approach in RCC is currently ongoing (National Cancer Institute; Antigenics, press release Dec. 22, 2003).

It is generally accepted that the main parameter to rate the prognosis of a RCC patient after surgery is the pathologic stage depicted by the TNM classification. The classification has been revised in 2002 as follows (11):

TABLE 3

TNM Classification

| | |
|---|---|
| T1 | Tumor $\leq$7 cm in greatest dimension, limited to the kidney |
| T1a | Tumor $\leq$4 cm in greatest dimension, limited to the kidney |
| T1b | Tumor >4 cm but $\leq$7 cm in greatest dimension, limited to the kidney |
| T2 | Tumor >7 cm in greatest dimension, limited to the kidney |
| T3 | Tumor invades into larger veins or adrenal gland or perinephric tissue but not beyond Gerota's fascia |
| T3a | Tumor directly invades adrenal gland or perirenal and/or renal sinus fat but not beyond Gerota's fascia |
| T3b | Tumor grossly extends into renal vein or its segmental (muscle-containing) branches, or vena cava below the diaphragm |
| T3c | Tumor grossly extends into the vena cava above the diaphragm or invades the wall of the vena cava |
| T4 | Tumor invades beyond Gerota's fascia |
| N0 | No regional lymph node metastasis |
| N1 | Metastases in a single regional lymph node |
| N2 | Metastasis in more than one regional lymph node |
| M0 | No distant metastasis |
| M1 | Distant metastasis |

In a patient collective of 675 patients with radical nephrectomy evaluated retrospectively in one hospital, 48% of the patients had pT1, 20% pT2, 10% pT3a, 20% pT3b and 2% pT4 (12).

The TNM classification only takes into consideration the macroscopically determinable invasion of vessels and surrounding tissues. Using multivariate statistical analysis it was found that the grade of anaplasia and microscopic vascular invasion (MVI) also provided prognostic information. The latter two variables are prognostically interconnected as MVI was particularly frequent among tumors with a high grade of anaplasia and less frequent in low grade tumors, with 56% vascular invasion for nuclear grading GII-GIII and 24% in GI tumors respectively. Patients with vascular invasion had a higher frequency of metastasis than those without (47% vs. 21%) (13).

Chimeric monoclonal antibody cG250 is a IgG1 kappa light chain chimeric version of an original murine monoclonal antibody mG250, first described by Oosterwijk et al. (22). Chimeric G250 (cG250) has been shown to be equivalent to murine mG250 in competitive binding assays and shows similar binding reactivities on human cancer cell lines as mG250. G250 detects a cell-surface antigen (MN antigen) on renal cancer cells. In immunohistochemical assays on sections of fresh frozen tissues, G250 reacts with 95% of renal cancers of the clear cell type and with a much lower proportion of colon cancers and other cancers. Reactivity with renal cancers is homogeneous (greater than 75% reactive cells) in 75% of renal cancers. The reactivity of cG250 with normal human tissues is restricted to the gastric epithelium and the biliary ducts in the liver (23, 24).

The chimeric antibody can be radiolabeled with Iodine-131 with minimal loss of immunoreactivity. In a study with 16 patients with metastatic RCC, $^{131}$I-labeled antibody was infused one week before nephrectomy (25). After infusion the radiolabeled antibody gradually localized into the tumor with the remainder being excreted from the body. The percentage of labeled antibody that localized into the tumor was among the highest ever reported in clinical trials with anti-tumor antibodies.

In a phase I multiple dose study with the unlabeled formulation of the cG250 antibody, 12 metastatic RCC patients received weekly doses for 6 weeks in a dose escalating setting. The results showed that the antibody is safe at all dose levels of 5, 10, 25 and 50 mg/m$^2$. One objective response was seen and 8 out of 12 patients presented with disease stabilization after the first 6-week-cycle of treatment (26).

In addition, in a phase II study where the unlabeled cG250 antibody was administered as monotherapy, 32 evaluable patients with metastatic RCC were treated up to 20 weeks with 50 mg cG250 once weekly. The study confirmed the excellent safety profile of long term treatment with the antibody. No serious drug related adverse events were reported and no allergic reactions occurred. In two patients very low human anti-chimeric antibody (HACA) levels were seen (27). Of the 32 patients, 6 patients who were progressive at study entry, achieved stabilization of disease for at least 6 months. In addition, two tumor regressions, one complete response and one minor response, were seen 4 months after the end of treatment in the follow up period. None of these patients received any tumor therapy in the meantime. The median overall survival was determined to be 15.6 months, with 35% of the patients still alive after a follow up time of up to 166 weeks. All studies have confirmed the excellent tolerability of cG250.

The mechanism of action of cG250 is antibody-dependent cellular cytotoxicity (ADCC), although other mechanism of actions may be possible. In vitro studies indicate that 0.5 µg/ml of cG250 is adequate for the induction of ADCC (28). This suggests that a clinical dosing regimen delivering levels of cG250 of at least 0.5 µg/ml should be efficacious, provided the drug is able to reach the target. In addition, the results from a dose escalation study using tracer doses of radiolabeled cG250 indicate that single doses above 10 mg per patient should be optimal for saturating all antigen positive tumor cells for a period of one week (24). These data indicate that plasma concentrations greater than 0.5 µg/ml would not offer additional clinical benefit.

As discussed above, new therapies have been approved in recent years for the treatment of metastatic RCC, the survival rates for renal cell carcinoma have not significantly changed for decades. Consequently, the problem underlying the present invention is the identification of new treatment options, in particular broad and easily applicable and non-toxic treatments for RCC patients with high risk for recurrence after nephrectomy with no evidence of macroscopically detectable disease.

The solution to the problem is the method of the present invention for the adjuvant therapy of patients wherein the primary tumor is characterized by G250 expression.

In one embodiment of the present invention, the method of treating a G250 antigen expressing cancer comprises administering a G250-antigen-specific antibody or/and an antibody fragment thereof as an adjuvant therapy to a patient with a primary tumor, wherein the patient has undergone primary tumor resection and, if necessary, lymphadenectomy and/or is due to undergo primary tumor resection and, if necessary, lymphadenectomy.

It is preferred that the patient has been diagnosed with non-metastatic disease or/and has been diagnosed as having a high risk of recurrence. Non-metastatic disease patients can be classified as risk groups I, II or III according to the classification of the present invention (see below). Preferably the primary tumor is a G250-antigen-expressing tumor, particularly selected from renal clear cell carcinoma, cervical carcinoma, biliary carcinoma, esophagus carcinoma, colorectal carcinoma and lung carcinoma.

Anti-G250 antibodies are for example described in EP-B-0 637 336, which is incorporated herein by reference.

In another preferred embodiment the antibody or/and the antibody fragment thereof is selected from the group consisting of polyclonal antibodies, monoclonal antibodies, antigen binding fragments thereof such as F(ab')$_2$, Fab', sFv, dsFv and chimerised, humanised and fully human variants thereof. Especially preferable, the antitumor antibody is chimeric or humanized G250 antibody and/or a fragment thereof. These antibodies may be produced by methods as described in PCT/EP02/01282 and PCT/EP02/01283, which are incorporated herein by reference. The most preferred antibody is cG250. Another most preferred antibody is the monoclonal antibody G250 produced by the hybridoma cell line DSM ACC 2526, a deposit of which has been made at the DSMZ, Mascheroder Weg 1b, D-38124 Braunschweig.

A more preferred embodiment is a method of treating renal clear cell carcinoma comprising administering a G250-antigen-specific antibody or/and an antibody fragment thereof as an adjuvant therapy to a patient with a primary tumor, wherein the patient has undergone primary tumor resection and, if necessary, lymphadenectomy and/or is due to undergo primary tumor resection and, if necessary, lymphadenectomy.

It is most preferred that the method of treating renal clear cell carcinoma of the present invention comprises administering the antibody cG250.

Tumor patients classified as belonging to one of the following risk groups, for example, have a high risk of recurrence. These risk groups refer to TNM classification, 6$^{th}$ edition UICC (2002):

Risk group I: the primary tumor has histologically proven stage T3bN0M0 or T3cN0M0 or T4N0M0

Risk group II: any histologically proven T stage and N1 or N2 disease

Risk group III: primary tumor T1bN0M0 or T2N0M0 or T3aN0M0, each with microscopic vascular invasion and grade III (Fuhrman or any other nuclear grading system with at least 3 grades)

A metastasis is the movement or spreading of cancer cells from one organ or tissue to another. Cancer cells usually spread via the bloodstream or the lymph system. With respect to the local relationship to the primary cancer, metastatis is differentiated between local metastasis (locally close or near to the primary cancer), regional metastasis (in the area of the regional lymph system) and distant metastasis.

Patients diagnosed with N0 and M0 can be classified as risk groups I or III. During the progression of cancer, lymphatic metastases may occur in a single regional lymph node (N1 according to TNM classification) or/and in more than one regional lymph node (N2) which is classified as high risk group II, wherein patients with distant metastases would be classified as metastatic disease. Therefore, in a preferred embodiment, the patients to be treated by the method of the present invention are patients with a high risk of recurrence, classified as risk group I, II or III.

The non-metastatic disease may have no histologically proven metastases in regional lymph nodes (N0 according to TNM) and no distant metastases (M0). There is, however, a considerable risk of recurrence in patients by tumor cells, e.g. in micrometastases, which have remained after primary tumor resection and which cannot be detected by histological methods, resulting in the diagnosis that the patient has no evidence of any residual tumor disease. In a preferred embodiment the patient with a high risk of recurrence to be treated by the method of the present invention has/has had a primary tumor classified as N0 and M0. In a more preferred embodiment, the N0 and M0 patient, after primary tumor resection and, optionally, lymphadenectomy, is diagnosed as having no evidence of any residual tumor disease.

Alternatively, the non-metastatic disease may have lymphatic metastases in a single regional lymph node (N1), or in more than one regional lymph node (N2). In a preferred embodiment of the present invention, the patient with a high risk of recurrence has/has had a primary tumor classified as N1 or N2.

The rationale for the selection of the risk groups of the present invention is as follows:

Risk Group I:

An analysis of the pT3 subgroups shows a significant decrease of the median survival as soon as Gerota's fascia is penetrated (transition between pT3a and pT3b). From a median survival of 107 months for pT3a, survival is reduced to 64 months for pT3b and to 30 months for pT3c (14). In addition, a prospective cohort study of 814 patients was performed in which RCC was subclassified into risk groups to predict clinical outcome. One group, named "non-metastatic high risk" (NM-HR) contained patients with non-metastatic, N0 tumors of T3 or greater and different combinations with other factors (performance scale, nuclear grading). This group with a relapse rate of approximately 42% at 24 months had a significantly worse prognosis than the intermediate and low risk group (7).

Risk Group II:

It has been shown in the past that the probability of relapse is significantly higher in node positive than in other patient categories. In the node positive group, 80% of patients relapsed within 30 months. Patients with node-negative disease had a much better prognosis, with only 40% relapsing at 3 years (15,16).

Risk Group III:

Several studies have addressed the presence of microscopic vascular invasion (MVI) for its prognostic value. Microscopic invasion was considered present when tumor was seen in a vessel, that is at least one or more endothelial cells of the tunica media of the vessel were recognized to surround a neoplastic cell group. Lang et al. have assessed this parameter in 255 N0M0 patients treated by radical nephrectomy during an observation period of at least 5 years following surgery (17). The presence of MVI was determined by a double blind histology study and was noted in 29% of the patients. In this study, MVI was not an independent and significant prognostic factor but it was related to an increased metastatic progression risk. Recently van Poppel has retrospectively analyzed 180 patients after radical or partial nephrectomy (18). The relevance of microscopic vascular invasion was compared to classical tumor staging, grade and tumor diameter. MVI was found in 28,3% of the patients. In patients with MVI but without lymph node involvement or macroscopic vascular invasion the risk of disease progression was at 45% within one year.

Since the presence of MVI cannot be considered to be a significant prognostic factor, patients who have undergone primary tumor resection and who do not exhibit MVI have to be regarded as patients with a high risk of recurrence. Therefore, in a preferred embodiment, the patients to be treated by the method of the present invention do not exhibit any histologically proven MVI.

In a further study, grade, vascular invasion and young age were identified as the main independent predictors for relapse in clinically localized RCC after nephrectomy (19).

With respect to grading, it was shown that high grade tumors (e.g. Fuhrman grade 3 and 4) have a poorer cancer specific survival as well as metastasis free survival than patients with low grade tumors (grade 1 and 2) (21).

The combination of MVI and grading is taken as a negative prognostic factor when concurrent with a tumor size greater 4 cm. Therefore, these patients also have to be regarded as patients with a high risk of recurrence. Supporting evidence comes from an assessment of 840 patients with pT1 renal cell carcinomas (20). This retrospective study supports the conclusion that a 7-cm tumor size cutoff for pT1 may be too large for patients with clear cell RCC and a transition to increased risk occurs at tumor sizes between 4.5 and 5 cm. At this size of tumor, a transition was noted from low (less than expected) to high (greater than expected) risk of death from RCC. Indeed, with the revision of the UICC TNM classification in 2002, the transition between pT1a and pT1b was set at 4 cm.

Therefore, in another preferred embodiment, the patients to be treated by the method of the present invention exhibit MVI. Due to the combination of MVI and grading, which can be taken as a negative prognostic factor, it is more preferred that the primary tumor of the patient to be treated by the method of the present invention exhibiting MVI has a nuclear grade of at least GIII.

In one preferred embodiment, the antibody of the present invention is administered in a monotherapy protocol.

In a further preferred embodiment, the antibody may be administered in a combination therapy protocol. The adjuvant antibody treatment may be combined with any other type of adjuvant therapy, e.g. adjuvant chemotherapy, adjuvant hormone therapy or/and adjuvant radiation therapy. More preferably, a cytokine may be co-administered together with the antibody in order to increase antibody dependent cellular cytotoxicity (ADCC) and/or to activate the immune system of the patient, e.g. the NK cells.

The cytokine is preferably selected from the group consisting of interleukins, e.g. IL-2,3,4,5, 6, 7, 8, 9, 10, 11, 12, 13, 14 and 15, interferons, e.g. IFN-alpha, IFN-beta and IFN-gamma, TNF-alpha, TNF-beta, nerve growth factor (NGF), ligands of CD40, FAS, CD27 and CD30, macrophage-inhibiting protein, Rantes, active fragments and pharmaceutically acceptable analogs and derivatives and mixtures thereof. More preferably the cytokine is selected from IL-2 and IFN-alpha.

The physician will determine the dosage of the G250-antigen-specific antibody based on age, weight and the severity of the disease, for example. A dosing regimen of either 20 mg or 50 mg cG250, for example, per patient on a weekly cycle will deliver concentrations above 0.5 µg/ml and therefore should be adequate for efficacy. Therefore, in a preferred embodiment, weekly doses of the G250-specific antibody of 5 to 250 mg/week, more preferably 10 to 100 mg/week and most preferably 20 mg/week to 50 mg/week are administered.

Pharmacokinetic data collected in above-mentioned state of the art studies indicate that trough plasma levels of cG250 reach a plateau level in six to ten weeks of treatment. It was found that, where the dose was 20 mg per week, the trough plasma levels out at 5.5 µg/ml after 10 weeks of treatment. Surprisingly, this is almost the same trough level (4.2 µg/ml) as that achieved one week following a single dose of 50 mg. This suggests that achieving steady-state plasma levels with a weekly dose of 20 mg is accelerated by giving a prior loading dose of 50 mg.

Therefore, the method of the present invention preferably comprises the administration of a G250-antigen-specific antibody or/and an antibody fragment thereof to a subject in need thereof in at least two treatment stages in which different, preferably decreasing, amounts of the antibody are administered.

It is more preferred that the method of the present invention comprises the administration of a G250-antigen-specific antibody or/and an antibody fragment thereof to a subject in need thereof in two stages, wherein
  (a) a dose of 10-250 mg/week, preferably 20-100 mg/week, more preferably 20-50 mg/week and most preferably 50 mg/week of the G250-antigen-specific antibody is administered in the first treatment stage and
  (b) a dose of 5-100 mg, preferably 10-50 mg, more preferably 15-25 mg, most preferably 20 mg/week of the G250-antigen-specific antibody is administered in the second treatment stage.

It is even more preferred that the first treatment stage comprises administration of 50 mg/week of the G250-specific antibody, and the second treatment stage comprises administration of 20 mg/week.

The antitumor antibody is preferably administered intravenously, preferably by infusion or intravenous injections. The administration of the antibody by infusion is preferably performed in up to about 30 minutes, more preferably in about 15 minutes.

Dosing schemes with weekly infusions of either 20 or 50 mg of cG250 for up to 20 weeks appear to be well tolerated and do not lead to significant HACA development.

It is therefore preferred that the first treatment stage comprises up to 12 weeks, preferably up to 6 weeks, even more preferably up to one week and the second treatment stage comprises up to 156 weeks, preferably up to 104 weeks, more preferably up to 52 weeks, even more preferably up to 12-24 weeks.

In the most preferred embodiment, the first treatment stage comprises up to one week and the administration of a single loading dose of 50 mg/week of cG250, and the second treatment stage comprises up to 24 weeks and the administration of 20 mg/week of cG250 for the treatment of renal clear cell carcinoma.

In yet another embodiment, the present invention relates to a pharmaceutical composition or kit comprising a G250-antigen-specific antibody or/and an antibody fragment thereof for administering in the method of the present invention as described above.

In a preferred embodiment, the pharmaceutical composition or kit comprises a first composition comprising the G250-antigen-specific antibody or/and an antibody fragment thereof for treatment in a first treatment stage, and further comprising a second composition comprising the G250-antigen-specific antibody or/and an antibody fragment thereof for treatment in a second treatment stage.

Furthermore, the present invention should be explained by the following example.

EXAMPLE 1

Clinical Trial Comprising the Adjuvant Antibody-cG250 Treatment in Patients with Clear Cell RCC and High Risk of Recurrence.

1.1 Design

This is a prospective, multi-center, phase III study to evaluate the efficacy and safety of adjuvant cG250 treatment versus placebo in clear cell RCC patients after surgery with no evidence of residual disease and with a high risk of recurrence.

The main objective is to evaluate the efficacy of the treatment by assessing the disease-free survival and overall survival in the treatment arm compared to the placebo arm. In addition, the safety of the antibody therapy and the impact on the quality of life is assessed.

1.2 Endpoint Criteria

The primary objectives are:
a) To evaluate disease-free survival on cG250 therapy as compared to placebo
b) To evaluate overall survival on cG250 therapy as compared to placebo The secondary objectives are:
c) To assess quality of life in the treatment and placebo arms using a validated questionnaire
d) To evaluate safety 1.3 Duration of the Study The duration of treatment for an individual patient in both arms is 24 consecutive weeks. Monitoring of survival will continue until 310 deaths have occurred or 60 months after the last patient has enrolled, whichever is the later.

1.4 Selection of Subjects Inclusion Criteria

Prior nephrectomy of primary renal cell carcinoma with documented clear cell histology
Adenectomy of regional lymph nodes and staging is required
No evidence of macroscopic and microscopic residual disease
Patients diagnosed of having one of the following (referring to TNM classification, 6th edition UICC, 2002):
histologically proven stage T3bN0M0 or T3cN0M0 or T4N0M0
any histologically proven T stage and N1 or N2 disease
primary tumor T1bN0M0 or T2N0M0 or T3aN0M0, each with microscopic vascular invasion and grade $\geq$III (Fuhrman or any other nuclear grading system with at least 3 grades)
ECOG of 0 (see Table II)
Not more than 6 weeks after nephrectomy
Negative HIV and hepatitis test
Negative pregnancy test for women of child-bearing potential (urine or serum)
Women of child-bearing potential must be taking adequate contraceptive precautions
Willingness to return to the study site for long term control visits until recurrence
Age $\geq$18 years
Ability to provide written informed consent

TABLE II

ECOG/Karnofsky Performance Scale

| ECOG Performance Status | | Karnofsky Performance Scale | |
| --- | --- | --- | --- |
| 0 | Fully active, able to carry on all pre-disease performance without restriction | 100 | Normal with no complaints or evidence of disease. |
| 1 | Restricted in physically strenuous activity but ambulatory and able to carry out work of a light or sedentary nature, e.g., light house work, office work. | 90 | Able to carry on normal activity but with minor signs of illness present. |
| | | 80 | Normal activity but requiring effort. Signs and symptoms of disease more prominent. |
| 2 | Ambulatory and capable of all self-care but unable to carry out any work activities. Up and about more than 50% of waking hours. | 70 | Able to care for self, but unable to work or carry on other normal activities. |
| | | 60 | Able to care for most needs, but requires occasional assistance. |
| 3 | Capable of only limited self care, confined to bed or chair more than 50% of waking hours. | 50 | Considerable assistance and frequent medical care required; some self-care possible. |
| 4 | Completely disabled, cannot carry on any self-care. Totally confined to bed or chair. | 40 | Disabled; requiring special care and assistance. |
| 5 | Dead. | 30 | Severely disabled; hospitalization required but death not imminent. |
| | | 20 | Extremely ill; supportive treatment and/or hospitalization required. |
| | | 10 | Imminent Death. |
| | | 0 | Dead. |

1.5 Study Medication

The study medication is administered once a week (plus or minus two days) by intravenous infusion on 24 consecutive weeks. A single loading dose of 50 mg of cG250 is administrated in week 1 followed by weekly infusions of 20 mg of cG250 in week 2-24. For the first administration in week 1 a total of 50 mg antibody as solution is dispensed. For all further consecutive administrations in weeks 2-24 a total of 20 mg antibody as solution is dispensed. The solution is withdrawn with a syringe and must be pre-filtered with the 0.2 μm filter before being added to 100 ml normal saline (sterile 0.9% sodium chloride in water). An additional 2 ml of normal saline is used to flush the filter to avoid loss of study medication in the filter. The normal saline, containing antibody, is injected into the infusion solution. Infusion is administered over 15 minutes with the patient seated or supine.

1.6 Assessment of Efficacy 1.6.1 Efficacy Parameters

A significantly better disease-free survival in the treatment arm compared to the placebo arm is considered proof of efficacy of the treatment. This is subsequently confirmed by determining the overall survival (median survival and 5-years-survival). Radiological assessment serves to document the presence of tumor recurrence. Two independent radiologic reviews for signs of metastatic disease or local recurrence centrally assess spiral CTs at baseline and during the course of the study.

1.6.2 Assessment of Disease-Free Survival

Assessment of tumor recurrence is based on contrast-enhanced spiral computer-tomography (CT) of the chest, abdomen and pelvis (venous phase) with a contiguous slice thickness of $\leq$7.5 mm performed in the radiology department of the study site. For quality reasons the scans are stored digitally on CD-ROM. In exceptional cases provision of data on film is acceptable, e.g. if digital data cannot be obtain at a certain assessment time point.

1.7 Statistics

The primary study endpoints are disease-free survival and overall survival.

Disease-free survival is calculated from the date of randomization up to the date of documented relapse. The median is reached when 50% of all patients have relapsed. Patients with no documented relapse are censored at the date of their last evaluation on study.

Relapse is defined as signs of metastatic disease or local recurrence as confirmed by computer tomography, death (excluding deaths unrelated to the disease) or start of new anti-tumor therapy.

Overall survival is calculated from the date of randomization to the date of documented death. Patients with no documented death are censored at the date of their last evaluation on study.

Secondary endpoints are:

Quality of life (EORTC QLQ-C30 questionnaire) The QLQ-C30 developed by the EORTC is composed of both multi-item scales and single-item measures (24, 25). These include five functional scales, three symptom scales, a global health status/QoL scale, and six single items. Each of the multi-item scales includes a different set of items—no item occurs in more than one scale. The statistical package for the coding of the scoring procedure has been provided by the EORTC and is performed in SAS.

Incidence of Clinical Adverse Events

Laboratory values graded in accordance with the NCI CTC criteria.

1.7.1 Statistical Model

Hierarchical testing is applied for disease-free survival and overall survival to keep the global significance level of 5%.

Disease-free survival, one of the primary study endpoints, is compared between the cG250 arm and the placebo arm using a group sequential log-rank test based on O'Brien and Fleming type boundary values at an overall 5% alpha level. Model estimates is derived using the Kaplan-Meier method. The primary analysis of disease-free survival is based upon the intent-to-treat population (defined as all patients randomized).

Overall survival, the other primary study endpoint, is compared between the cG250 arm and the placebo arm using the log-rank test and the Kaplan-Meier method. The significance levels within the analyses of overall survival is adjusted using the O'Brien-Fleming approach for group sequential methods to keep the overall significance level to 5%. The primary analysis of overall survival is based upon the intent-to-treat population (defined as all patients randomized).

The 95% confidence interval for proportions is calculated using the exact method (Pearson-Clopper).

Kaplan-Meier curves for disease-free survival and overall survival are displayed by treatment group. Descriptive statistics are used. Missing values are not replaced.

The potential effect of prognostic factors on both disease-free survival and overall survival is investigated using the Cox proportional hazard model for time to event parameters. The objective is to explore the sensitivity of the statistical significance after adjusting for main prognostic factors. The main parameters that are deemed to have potential prognostic value are reflected in the TNM classification and the stage of disease at study entry. The three high-risk criteria as defined at study entry adequately reflect risk factors with prognostic value identified in renal cell carcinoma to date.

Separate stratification of U.S. and European sites are performed.

All efficacy analyses are performed using the intention-to-treat population as primary analysis set and are repeated using the per protocol population.

Secondary statistical analysis tests are performed at an alpha level of 5% and are regarded as exploratory, therefore no adjustment for multiplicity are made.

REFERENCES

1. Liao et al. Identification of the MN antigen as a diagnostic biomarker of cervical intraepithelial squamous and glandular neoplasia and cervical carcinomas. Am J, Pathol. 145, 598-609 (1994).
2. Turner et al., Hum. Pathol. MN antigen expression in normal, preneoplastic, and neoplastic esophagus: a clinicopathological study of a new cancer-associated biomarker. 28, 740-744 (1997).
3. Saarnio et al. Immunohistochemical study of colorectal tumors for expression of a novel transmembrane carbonic anhydrase, MN/CAIX, with potential value as a marker of cell proliferation. Am. J. Pathol. 153, 279-285 (1998).
4. Vermylen et al. Carbonic anhydrase IX antigen differentiates between preneoplastic malignant lesions in non-small cell lung carcinoma. Eur. Respir. J. 14, 806-811 (1999).
5. Saarnio et al. Transmembrane carbonic anhydrase, MN/CAIX, is a potential biomarker for biliary tumors. 35, 643-649 (2001).
6. DeVita V. T. & Hellman, S. R. S. A. Cancer: principles and practice of oncology. Lippincott Williams & Wilkins (2001).
7. Zisman, A. et al. Risk group assessment and clinical outcome algorithm to predict the natural history of patients with surgically resected renal cell carcinoma. J. Clin. Oncol. 20, 4559-4566 (2002).
8. Lipton, A. Effects of Renal Cell Carcinoma on the Skeleton. Perry, M. American Society of Clinical Oncology Educational Book (38th annual meeting), 633-634. 2002. American Society of Clinical Oncology.
9. Pizzocaro, G. et al. Interferon adjuvant to radical nephrectomy in Robson stages II and III renal cell carcinoma: a multicentric randomized study. J. Clin. Oncol. 19, 425-431 (2001).
10. Dutcher, J. P. Introduction to the session on integration of immunotherapy and surgery in metastatic renal cell carcinoma. Piantadosi, S. American Socity of Clinical Oncology Educational Book (38th annual meeting), 630-632, 2002. American Society of Clinical Oncology.
11. Sobin, L. & Wittekind, C. TNM Classification of Malignant Tumors, 6th edition. John Wiley & Sons (2002).
12. Ficarra, V. et al. Prognostic factors in patients with renal cell carcinoma: retrospective analysis of 675 cases. Eur. Urol. 41, 190-198 (2002).
13. Sanchez, d. I. M. et al. Renal cell carcinoma: vena caval invasion and prognostic factors. Eur. Urol. 19, 284-290 (1991).
14. Hermanek, P. & Schrott, K. M. Evaluation of the new tumor, nodes and metastases classification of renal cell carcinoma. J. Urol. 144, 238-241 (1990).
15. Mulders, P. F. & De Mulder, P. H. The role of adjuvant immunotherapy in renal cell carcinoma. Curr. Urol. Rep. 3, 44-49 (2002).
16. Porzsolt, F. Adjuvant therapy of renal cell cancer with interferon-alpha. Delta-p gruppe. Proc. Am. Soc. Clin. Oncol. 11, 202 (1992).
17. Lang, H. et al. Microscopic venous invasion: a prognostic factor in renal cell carcinoma. Eur. Urol. 38, 600-605 (2000).

18. Van Poppel, H. et al. Microscopic vascular invasion is the most relevant prognosticator after radical nephrectomy for clinically non-metastatic renal cell carcinoma. J. Urol. 158, 45-49 (1997).
19. Griffiths, D. F. et al. Contribution of grade, vascular invasion and age to outcome in clinically localized renal cell carcinoma. BJU. Int. 90, 26-31 (2002).
20. Lau, W. K., Cheville, J. C., Blute, M. L., Weaver, A. L. & Zincke, H. Prognostic features of pathologic stage T1 renal cell carcinoma after radical nephrectomy. Urology 59, 532-537 (2002).
21. Fuhrman, S. A., Lasky, L. C. & Limas, C. Prognostic significance of morphologic parameters in renal cell carcinoma. Am. J. Surg. Patholog. 6, 655-663 (1982).
22. Oosterwijk, E. et al. Monoclonal antibody G 250 recognizes a determinant present in renal-cell carcinoma and absent from normal kidney. Int. J. Cancer 38, 489-494 (1986).
23. Oosterwijk, E. et al. Antibody localization in human renal cell carcinoma: a phase I study of monoclonal antibody G250. J. Clin. Oncol. 11, 738-750 (1993).
24. Steffens, M. G. et al. Targeting of renal cell carcinoma with iodine-131-labeled chimeric monoclonal antibody G250. J. Clin. Oncol. 15, 1529-1537 (1997).
25. Wiseman, G. A. Chimeric G250 monoclonal antibody (cG250) Phase I dose escalation trial in patients with advanced renal cell carcinoma (RCC). ASCO Meeting San Francisco May 2001 (2001).
26. Beck, J. et al. A phase II trial with monoclonal antibody WX-G250 in advanced RCC. 2nd International Kidney Cancer Symposium Chicago 2001. 30 Oct. 2001.
27. Surfus, J. et al. Anti-renal-cell carcinoma chimeric antibody G250 facilitates antibody-dependent cellular cytotoxicity with in vitro and in vivo interleukin-2-activated effectors. J. Immunother. 19, 184-191 (1996).
28. Steffens, M. G. et al. Phase I radioimmunotherapy of metastatic renal cell carcinoma with 131I-labeled chimeric monoclonal antibody G250. Clin. Cancer Res. 5, 3268s-3274s (1999).
29. Aaronson, N. K. et al. The European Organization for Research and Treatment of Cancer QLQ-C30: a quality-of-life instrument for use in international clinical trials in oncology. J. Natl. Cancer Inst. 85, 365-376 (1993).
30. Fayers, P. M. et al. The EORTC QLQ-C30 Scoring Manual (3rd Edition). European Organisation for Research and Treatment of Cancer, Brussels (2001).
31. Manual, Tumorzentrum München, 3. Edition 2003 W. Zuckschwerdt, München Wien New York Editor B. Liedl
32. John N. Eble, M.D. and Stephan Storkel, M.D. on the USCAP web site Apr. 24, 2001 www.palpath.com

The invention claimed is:

1. A method of treating a G250 antigen expressing cancer comprising administering a G250-antigen-specific antibody and/or an antibody fragment thereof as an adjuvant therapy to a patient with a primary tumor and wherein the patient has been diagnosed with non-metastatic disease, wherein the patient has undergone primary tumor resection and, if necessary, lymphadenectomy and/or is due to undergo primary tumor resection and, if necessary, lymphadenectomy.

2. The method of claim 1, wherein the patient has been diagnosed as having a high risk of recurrence.

3. The method according to claim 1, wherein the primary tumor is a G250-antigen-expressing tumor,-selected from the group consisting of renal clear cell carcinoma, cervical carcinoma, biliary carcinoma, esophagus carcinoma, colorectal carcinoma and lung carcinoma.

4. The method of claim 1, wherein the antibody or/and the antibody fragment thereof is selected from the group consisting of polyclonal antibodies, monoclonal antibodies, antigen binding fragments thereof such as F(ab')2, Fab', sFv, dsFv and chimerised, humanised and fully human variants thereof.

5. The method of claim 1, wherein the primary tumor has been classified as N0 and M0 according to the TNM classification.

6. The method of claim 5, wherein, after primary tumor resection and, optionally, lymphadenectomy, the patient is diagnosed as having no evidence of any residual tumor disease.

7. The method of claim 1, wherein the primary tumor has been classified as N1 or N2 according to the TNM classification.

8. The method of claim 1, wherein the primary tumor does not exhibit microvascular invasion.

9. The method of claim 1, wherein the primary tumor exhibits microvascular invasion.

10. The method of claim 9, wherein the primary tumor exhibits a nuclear grade of at least GIII.

11. The method of any of claim 1, wherein the patient to be treated is classified as risk groups I, II or III.

12. The method of claim 1, comprising the administration of a G250-antigen-specific antibody or/and an antibody fragment thereof to a subject in need thereof in at least two treatment stages in which different, preferably decreasing, amounts of the antibody are administered.

13. The method of claim 12, comprising the administration of a G250-antigen-specific antibody or/and an antibody fragment thereof to a subject in need thereof, wherein
   (a) a dose of 10-250 mg/week, preferably 20-100 mg/week, more preferably 20-50 mg/week and most preferably 50 mg/week of the G250-antigen-specific antibody is administered in a first treatment stage and
   (b) a dose of 5-100 mg, preferably 10-50 mg, more preferably 15-25 mg, most preferably 20 mg/week of the anti-G250 antibody is administered in a second treatment stage.

14. The method of claim 1, wherein the G250-antibody or/and antibody fragment is administered via an intravenous route.

15. The method of claim 14, wherein the intravenous administration is an infusion preferably performed over a period of up to about 30minutes, more preferably about 15 minutes.

16. The method of claim 12, wherein the first treatment stage comprises up to 12 weeks, preferably up to 6 weeks, even more preferably up to one week and the second treatment stage comprises up to 156 weeks, preferably up to 104 weeks, more preferably up to 52 weeks, even more preferably up to 12-24 weeks.

17. The method of claim 1, wherein the cancer is renal clear cell carcinoma.

18. The method of claim 1, wherein the antibody is cG250 or an antibody produced by the hybridoma cell line DSM ASC 2526.

* * * * *